(12) United States Patent
Stahurski et al.

(10) Patent No.: US 9,421,039 B2
(45) Date of Patent: Aug. 23, 2016

(54) APPARATUS FOR RETAINING BONE

(75) Inventors: Terrence Stahurski, Seven Hills, OH (US); Spanky A. Raymond, Uniontown, OH (US)

(73) Assignee: APPLIED ORTHOPAEDICS LLC, Seven Hills, OH (US)

( * ) Notice: Subject to any disclaimer, the term of this patent is extended or adjusted under 35 U.S.C. 154(b) by 158 days.

(21) Appl. No.: 13/504,629

(22) PCT Filed: Nov. 9, 2010

(86) PCT No.: PCT/US2010/055892
§ 371 (c)(1),
(2), (4) Date: Apr. 27, 2012

(87) PCT Pub. No.: WO2011/057227
PCT Pub. Date: May 12, 2011

(65) Prior Publication Data
US 2012/0215268 A1    Aug. 23, 2012

Related U.S. Application Data (60) Provisional application No. 61/259,252, filed on Nov. 9, 2009.

(51) Int. Cl.
*A61B 17/70*    (2006.01)
(52) U.S. Cl.
CPC ......... *A61B 17/7032* (2013.01); *A61B 17/7056* (2013.01)
(58) Field of Classification Search
CPC ........... A61B 17/7032; A61B 17/7085; A61B 17/7091; A61B 17/7064; A61B 17/7047; A61B 17/7056; A61B 17/7068; A61B 17/707; A61B 17/7076

USPC ............ 606/54–59, 246, 250–264, 276–278, 606/324, 330
See application file for complete search history.

(56) References Cited

U.S. PATENT DOCUMENTS

| 5,545,167 | A |   | 8/1996  | Lin |
| 5,562,662 | A | * | 10/1996 | Brumfield .......... A61B 17/7002 606/279 |
| 5,575,792 | A | * | 11/1996 | Errico et al. .................. 606/276 |
| 5,928,231 | A | * | 7/1999  | Klein et al. ..................... 606/60 |
| 5,961,517 | A | * | 10/1999 | Biedermann et al. ....... 606/86 A |
| 6,387,097 | B1 | * | 5/2002  | Alby ............................. 606/277 |
| 6,656,180 | B2 |   | 12/2003 | Stahurski |

(Continued)

FOREIGN PATENT DOCUMENTS

FR    2904526    8/2008
WO    2007/087486    8/2007

*Primary Examiner* — Eduardo C Robert
*Assistant Examiner* — Michelle C Eckman
(74) *Attorney, Agent, or Firm* — Tarolli, Sundheim, Covell & Tummino LLP (57) ABSTRACT

An apparatus (20) for use in retaining bone in a desired spatial relationship includes a rod (22) and a housing (26) that has a passage (24) through which the rod (22) extends along an axis (29). A connector (42) extends from the housing (26) and engages a bone. The connector (42) is movable relative to the housing (26) into any one of a plurality of positions. A locking member (68) is deflectable between a first condition for allowing relative movement between the connector (42) and the housing (26) and a second condition engaging the connector (42) to hold the connector (42) in any one of the plurality of positions relative to the housing (26).

38 Claims, 5 Drawing Sheets

(56) References Cited

U.S. PATENT DOCUMENTS

| | | |
|---|---|---|
| 2003/0045876 A1* | 3/2003 | Stahurski .................... 606/61 |
| 2004/0133206 A1* | 7/2004 | Stevens et al. ............... 606/72 |
| 2004/0236330 A1* | 11/2004 | Purcell et al. ................ 606/61 |
| 2006/0167458 A1* | 7/2006 | Gabele ........................ 606/72 |
| 2006/0200128 A1* | 9/2006 | Mueller ....................... 606/61 |
| 2006/0276789 A1* | 12/2006 | Jackson ....................... 606/61 |
| 2007/0016189 A1* | 1/2007 | Lake et al. ................... 606/61 |
| 2007/0072459 A1* | 3/2007 | Stahurski et al. ............ 439/135 |
| 2007/0090238 A1 | 4/2007 | Justis |
| 2008/0221621 A1* | 9/2008 | Snyder et al. ................ 606/263 |
| 2009/0105770 A1 | 4/2009 | Berrevoets et al. |
| 2011/0301646 A1* | 12/2011 | Kretzer et al. ................ 606/264 |
| 2013/0231704 A1* | 9/2013 | Larroque-Lahitette ....... 606/277 |

\* cited by examiner

APPARATUS FOR RETAINING BONE

CROSS-REFERENCES TO RELATED APPLICATIONS

This application claims priority to U.S. Patent Application Ser. No. 61/259,252, filed Nov. 9, 2009, the entirety of which is incorporated herein by reference.

TECHNICAL FIELD

The present invention relates to an apparatus for use in retaining bone in a desired spatial relationship and, in particular, relates to an adjustable apparatus that has a locking member for locking the position of the apparatus.

BACKGROUND OF THE INVENTION

The present invention relates to an apparatus for use in retaining bone in a desired spatial relationship. The apparatus may, for example, retain vertebrae of a spinal column in a desired spatial relationship. A known apparatus for retaining vertebrae of a spinal column in a desired spatial relationship includes a longitudinally extending member or rod which extends along the spinal column. A connector is connected with a housing of the apparatus by a pair of fasteners which engage opposite sides of the housing. A portion of a vertebra extends between the connector and the housing. An apparatus having this construction is disclosed in U.S. Pat. No. 6,656,180.

SUMMARY OF THE INVENTION

In accordance with an embodiment of the present invention, an apparatus for use in retaining bone in a desired spatial relationship includes a rod and a housing that has a passage through which the rod extends along an axis. A connector extends from the housing and engages a bone. The connector is movable relative to the housing into any one of a plurality of positions. A locking member is deflectable between a first condition for allowing relative movement between the connector and the housing and a second condition engaging the connector to hold the connector in any one of the plurality of positions relative to the housing.

In accordance with another aspect of the present invention, an apparatus for use in retaining bone in a desired spatial relationship include a rod and a housing that has a passage through which the rod extends. A connector extends from the housing and engages a bone. The connector is movable relative to the housing into any one of a plurality of positions. A locking member extends within the passage. The locking member has a first condition allowing relative movement between the connector and the housing, a second condition releasably holding the connector in any one of the plurality of positions relative to the housing, and a third condition preventing the connector from moving relative to the housing.

In accordance with another aspect of the present invention, an apparatus for use in retaining bone in a desired spatial relationship includes a rod and a housing that has a passage through which the rod extends along an axis. A connector extends from the housing and engages a bone. The connector is movable relative to the housing into any one of a plurality of positions. A locking member engages the connector to releasably hold the connector in any one of the plurality of positions. The connector is movable to any of the plurality of positions by applying a predetermined force to the connector.

BRIEF DESCRIPTION OF THE DRAWINGS

The foregoing and other features of the present invention will become more apparent upon a consideration of the following description taken in connection with the accompanying drawings wherein.

DETAILED DESCRIPTION

Figure 1:
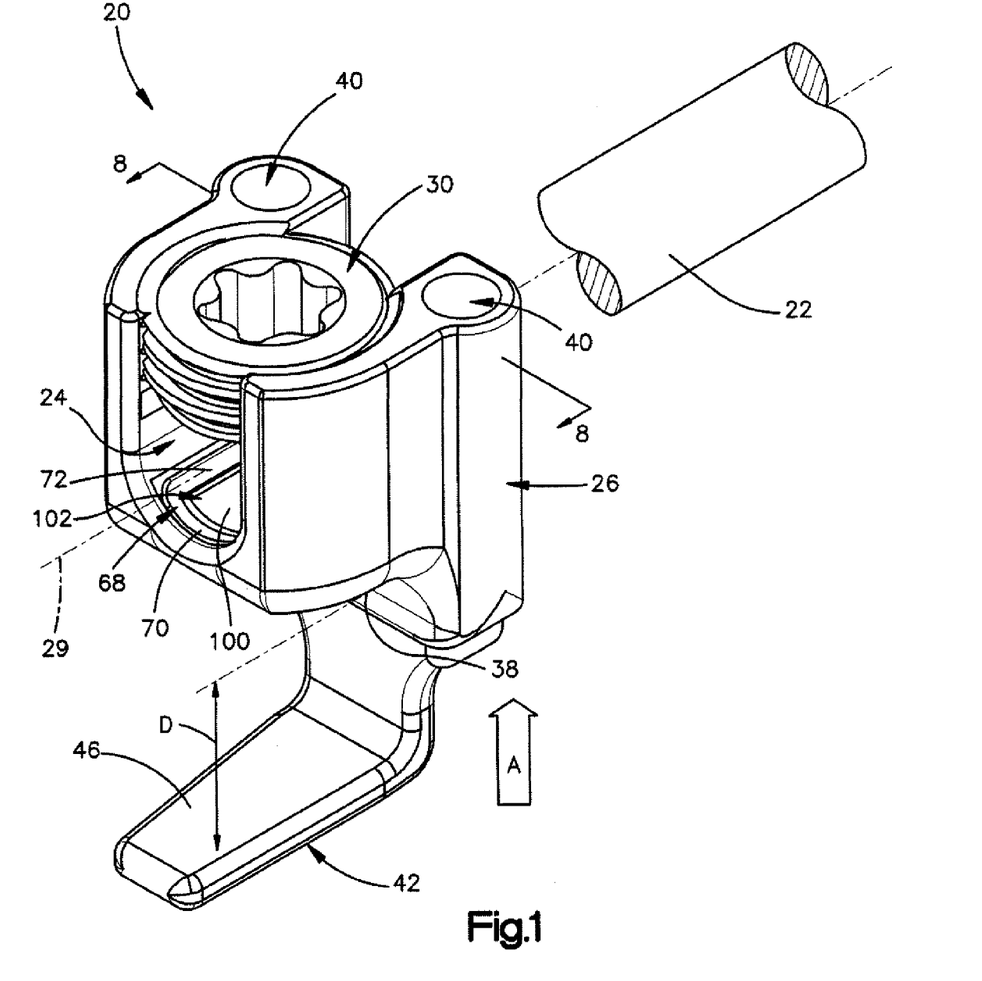
FIG. 1 is a schematic illustration of an apparatus for retaining vertebrae of a spinal column in a desired spatial relationship constructed in accordance with the present invention.
Figure 2:
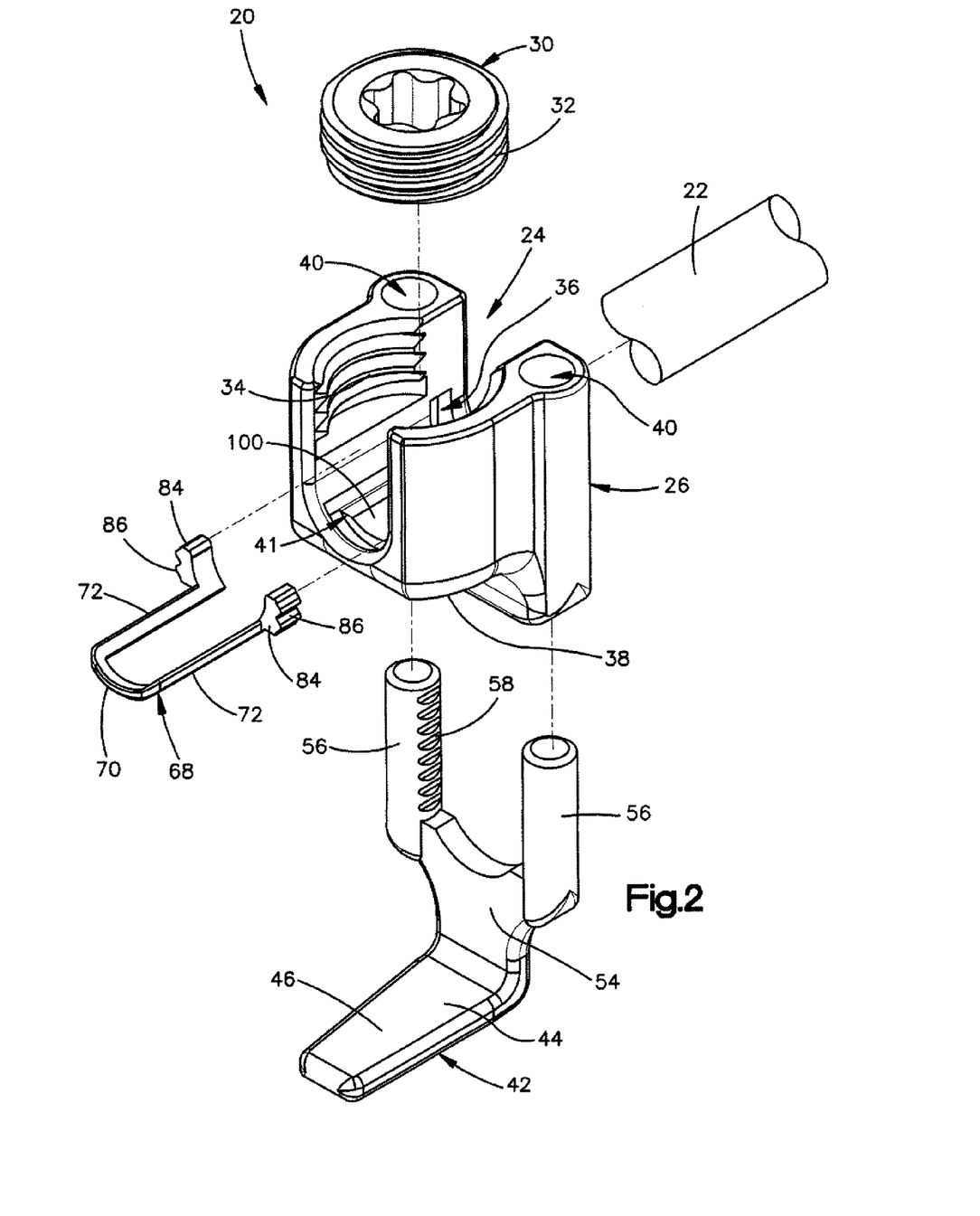
FIG. 2 is an exploded illustration of the apparatus of FIG. 1.

The present invention relates to an apparatus for use in retaining bone in a desired spatial relationship, such as a vertebral fixation device, and, in particular, relates to an adjustable apparatus that has a locking member for locking the position of the apparatus. The device may be used to fix bones near the spinal column, such as vertebrae and/or ribs. FIGS. 1-2 illustrate an apparatus or vertabral fixation device 20 for retaining vertebrae of a spinal column in a desired spatial relationship in accordance with an embodiment of the present invention. The apparatus 20 includes a rod 22, a housing 26, a connector 42, a locking member 68, and a clamping member 30.

The connector 42 is movable within and relative to the housing 26 into any one of a plurality of positions in order to secure or position a vertebra between the connector and the housing. The locking member 68 is secured to the housing 26 and the connector 42 and releasably holds the connector in any one of the plurality of positions relative to the housing. The rod 22 is positioned within a portion of the housing 26 overlying the locking member 68. The clamping member 30 is secured to the housing 26 to clamp the rod 22 within the housing. The clamping member 30 may engage the rod 22 to fix the rod to the locking member 68 to prevent relative movement between the rod, the housing 26, the connector 42, and the locking member and thereby lock the connector in any one of the plurality of positions relative to the housing.

The apparatus 20 may be formed of any desired biocompatible material. If desired, the apparatus 20 may be formed of a polymeric material. Alternatively or additionally, the apparatus 20 may be formed of a biocompatible metal, e.g., titanium.

The rod 22 has an elongated shape and extends along the spinal column or bone (not shown). The rod 22 may have a contour that corresponds with a desired contour of the spinal column or bone. The rod 22 may, for example, have an arcuate contour or may have a straight contour. The rod 22 may have a circular cross-section as shown in FIG. 1 or may have alternative cross-sections, such as triangular, square or any other polygonal shape (not shown). If desired, the cross-sectional area of the rod 22 may vary along its length.

Figure 3:
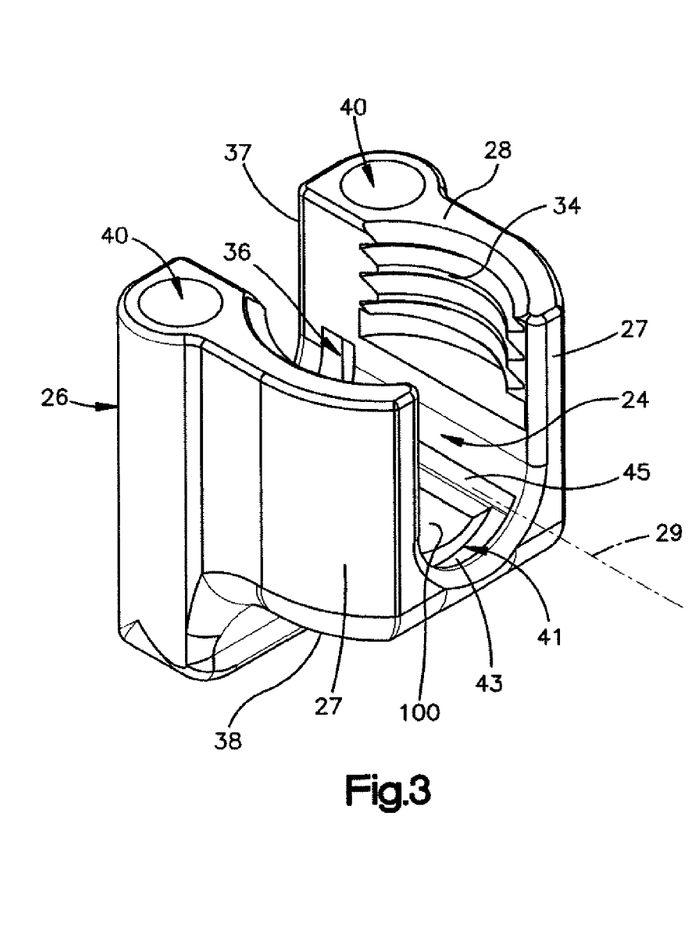
FIG. 3 is a schematic illustration of a housing of the apparatus of FIG. 1.

As shown in FIG. 3, the housing 26 is generally U-shaped. Alternatively, the housing 26 may have another shape, such as cylindrical or tubular (not shown). The housing 26 includes a pair of side walls 27 defining a passage 24 for receiving the rod 22. Each side wall 27 extends between an upper surface 28 and a lower surface 38 of the housing 26. Although the terms "upper" and "lower" have been used to designate portions of the housing 24, it will be understood that those spatial designations are relative to FIG. 3, and that alternative spatial designations could be used if the housing has a spatial orientation different from FIG. 3.

The passage 24 is substantially U-shaped and extends along an axis 29 through the entire housing 26. The cross-section of the passage 24 is sized to be larger than the cross-section of the rod 22 and can be designed to accommodate any sized rod. The passage 24 extends from the upper surface 28 of the housing 26 towards the lower surface 38 and terminates at a surface 100 positioned between the upper surface and the lower surface. The surface 100 is configured to have a contour that mirrors the periphery of the rod 22. The surface 100 may, for example, have a concave contour that corresponds with a circular rod 22. Alternatively, the surface 100 may have a shape that corresponds with the shape of a non-circular rod 22 (not shown). Portions of the side walls 27 adjacent to the surface 100 may also be configured similar to periphery of the rod 22.

An opening 40 extends through one or both side walls 27. As shown in FIG. 3, an opening 40 extends through each side wall 27 from the lower surface 38 to the upper surface 28 of the housing 26 such that the openings 40 are substantially parallel to one another. Alternatively, each opening 40 may extend from the lower surface 38 and terminate prior to the upper surface 28 (not shown). Although the openings 40 are shown as being generally circular, it is contemplated that the openings may have any cross-sectional shape.

Figure 4:
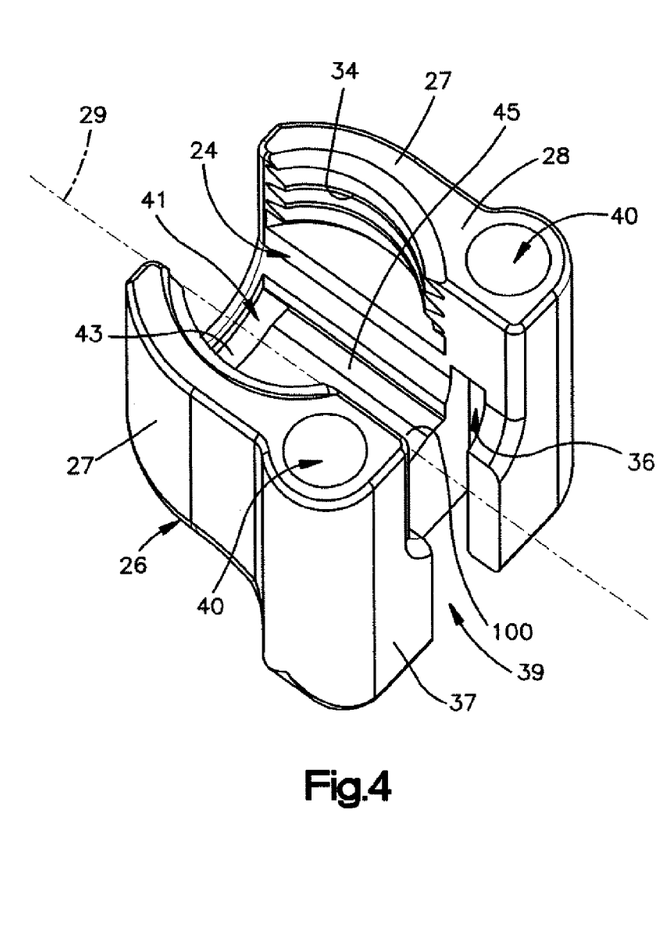
FIG. 4 is a schematic illustration of the housing showing a slot in the housing.

Referring to FIGS. 3-4, a slot 36 extends from the lower surface 38 of the housing toward the upper surface 28 and into communication with the passage 24. The slot 36 is spaced from a rear surface 37 of the housing 26. The slot 36 is positioned between and is substantially aligned with the openings 40 in the side walls 27 and is configured to communicate with a portion of each opening. The slot 36, the passage 24, and the openings 40 therefore communicate with one another. In particular, the slot 36 extends from the passage 24, into each side wall 27, and into communication with each opening 40. A notch 39 (FIG. 4) is formed in the rear surface 37 of the housing 26 and extends in a direction parallel to the axis 29 and into communication with the slot 36.

An internal thread convolution 34 is formed in each side wall 27 and extends from the upper surface 28 towards the concave surface 100, terminating prior to the concave surface. The thread convolution 34 is thereby formed in the passage 24 of the housing 26. The thread convolution 34 is configured to threadably receive the clamping member 30 for retaining the rod 22 within the passage 24. The thread convolution 34 may constitute square threads, helical threads or the like.

The housing 26 further includes a recess 41 for receiving the locking member 68 to hold the connector 42 in a desired position relative to the housing 24. The recess 41 includes an arcuate portion 43 and one or more straight portions 45. The arcuate portion 43 has a concave configuration and extends between the side walls 27. The arcuate portion 43 is positioned at an end of the passage 24 opposite the slot 36 and extends from the concave surface 100 towards the lower surface 38.

As shown in FIG. 4, a pair of straight portions 45 extends from the arcuate portion 43 to the slot 36 on opposite sides of the passage 24. Each straight portion 45 extends substantially parallel to the axis 29 and is positioned between the concave surface 100 and one of the side walls 27. The straight portions 45 may have an L-shaped cross-section or an arcuate cross-section (not shown). Although FIG. 4 illustrates that the recess 41 includes a pair of straight portions 45, those having ordinary skill will appreciate that the straight portions may alternatively be formed as arcuate portions such that the recess exhibits a rounded or C-shape (not shown).

Referring to FIG. 2, the clamping member 30 includes a set screw that has an external thread convolution 32 which engages the internal thread convolution 34 on each side wall 27. The position of the clamping member 30 relative to the housing 26 can be adjusted by rotating the clamping member relative to the housing. In particular, rotation of the clamping member 30 in a first direction relative to the housing 26 causes the clamping member to move toward the concave surface 100 while rotation of the clamping member in a second, opposite direction relative to the housing causes the clamping member to move away from the concave surface. The position of the clamping member 30 relative to the housing 26 is adjusted to clamp the rod 22 to the housing 26.

Figure 5:
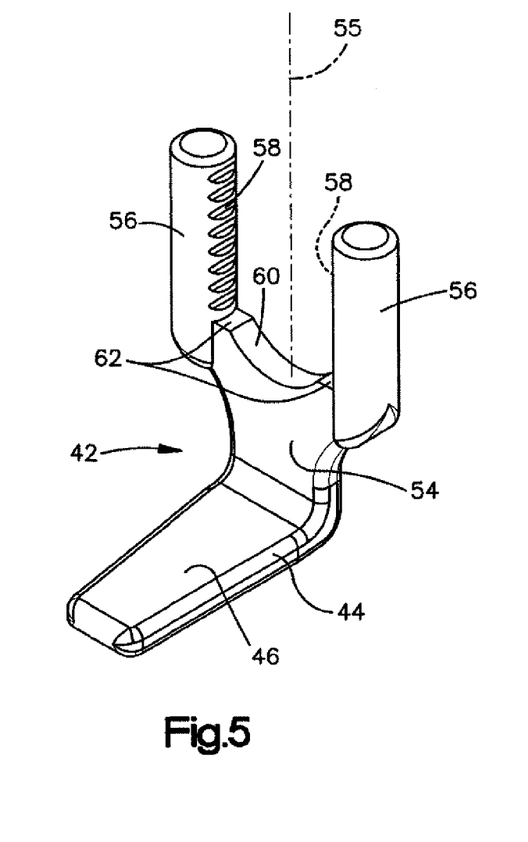
FIG. 5 is a schematic illustration of a connector of the apparatus of FIG. 1.

As shown in FIG. 5, the connector 42 is a hook that engages the bone or vertebra by, for example, capturing the bone or vertebra or other anatomic structure between the lower surface 38 of the housing 26 and the surface 46 of the connector 42. Alternatively, the connector 42 may be configured to penetrate the vertebra, e.g., the connector may include a screw thread which engages the vertebra (not shown). The connector 42 is substantially L-shaped and includes a base 44 having an upper surface 46 adapted to engage a vertebra. Although the surface 46 is shown as being rectangular, the surface may have any desired shape to accommodate any anatomical structure. The surface 46 may have texturing or other securing mechanism, such as teeth, for better attachment to the bone of the vertebra or other anatomic structure.

A central portion 54 of the connector 42 extends along an axis 55 and away from the upper surface 46 of the base 44. Although the central portion 54 is shown as extending generally perpendicular to the base 44, the central portion may extend at any desired angle relative to the base to accommodate any anatomical structure. The central portion 54 terminates at a surface 60 that is configured to have the same shape as the surface 100 on the housing 26 and, thus, in the illustrated embodiment, the surface has an upwardly facing concave shape. A pair of planar stop surfaces 62 is positioned on opposite sides of the surface 60.

One or more extensions or arms 56 extend from the central portion 54 in a direction away from the upper surface 46 and substantially parallel to the axis 55. The number of extensions 56 corresponds with the number of openings 40 in the housing 26. In the illustrated embodiment, the connector 42 includes two extensions 56. The extensions 56 are sized and shaped to extend into the openings 40 in the housing 26 and be moveable within the openings. The extensions 56 may have the same cross-sectional shape as the openings 40 in the housing 26. Each of the extensions 56 includes engaging members or teeth 58. The teeth 58 are located along inner portions of the extensions 56 such that the teeth of one arm face the teeth on the opposing arm. Alternatively, only one of the extensions 56 may have teeth 58 (not shown).

Figures 6, 7:
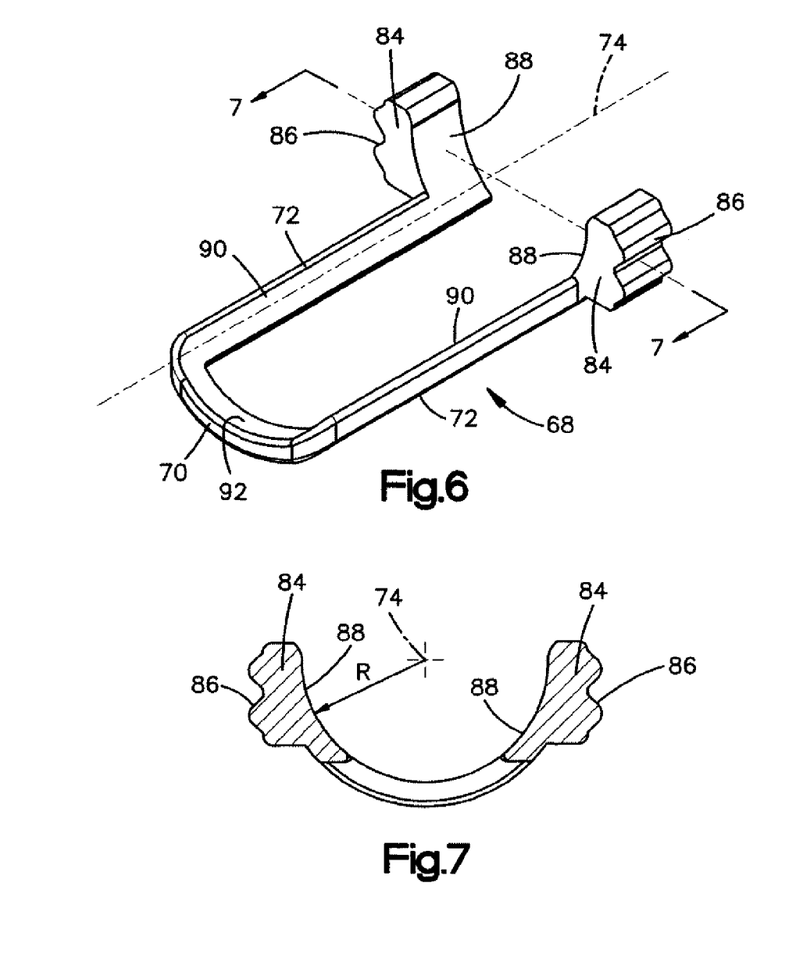
FIG. 6 is a schematic illustration of a locking member of the apparatus of FIG. 1.
FIG. 7 is a sectional view taken along line 7-7 of FIG. 6.

Referring to FIGS. 6 and 7, the locking member or clip 68 engages the housing 26 and the connector 42 to lock the connector in any one of the plurality of desired positions relative to the housing. The locking member 68 is generally U-shaped. The locking member 68 includes a base portion 70 and one or more deflectable arms 72 that extend from the base portion and are sized to be accommodated in the straight portions 45 of the recess 41 in the housing 26. In a construction in which the straight portions 45 of the recess 41 are arcuate, the arms 72 of the locking member 68 are also arcuate (not shown).

The number of arms 72 corresponds with the number of extensions 56 on the connector 42. In the illustrated embodiment, the locking member 68 includes a pair of arms 72. The locking member 68 is formed from a deflectable or resilient material such that the arms 72 of the locking member may be deflected toward or away from each other and relative to the base portion 70 when a predetermined force is applied to the arms.

Each arm 72 terminates at an upwardly extending locking portion 84. Each locking portion 84 includes engaging members or teeth 86 that extend outward. The teeth 86 of the locking portions 84 are configured to mate with the teeth 58 on the extensions 56 of the connector 42. Therefore, where only one extension 56 of the connector 42 includes teeth 58, only one of the arms 72 of the locking member 68 includes a locking portion 84 with teeth 86 (not shown).

As shown in FIG. 7, each locking portion 84 includes a generally concave inner surface 88. Each concave inner surface 88 has a radius designated by the arrow R measured from an axis 74. The radius R corresponds with the curvature of the rod 22 and the concave surface 100 of the housing 26. The remainder of each arm 72 and the base portion 70 likewise include inwardly facing concave upper surfaces 90 and 92, respectively, which have a radius that corresponds with the curvature of the rod 22 and the concave surface 100 of the housing 26.

Figure 8:
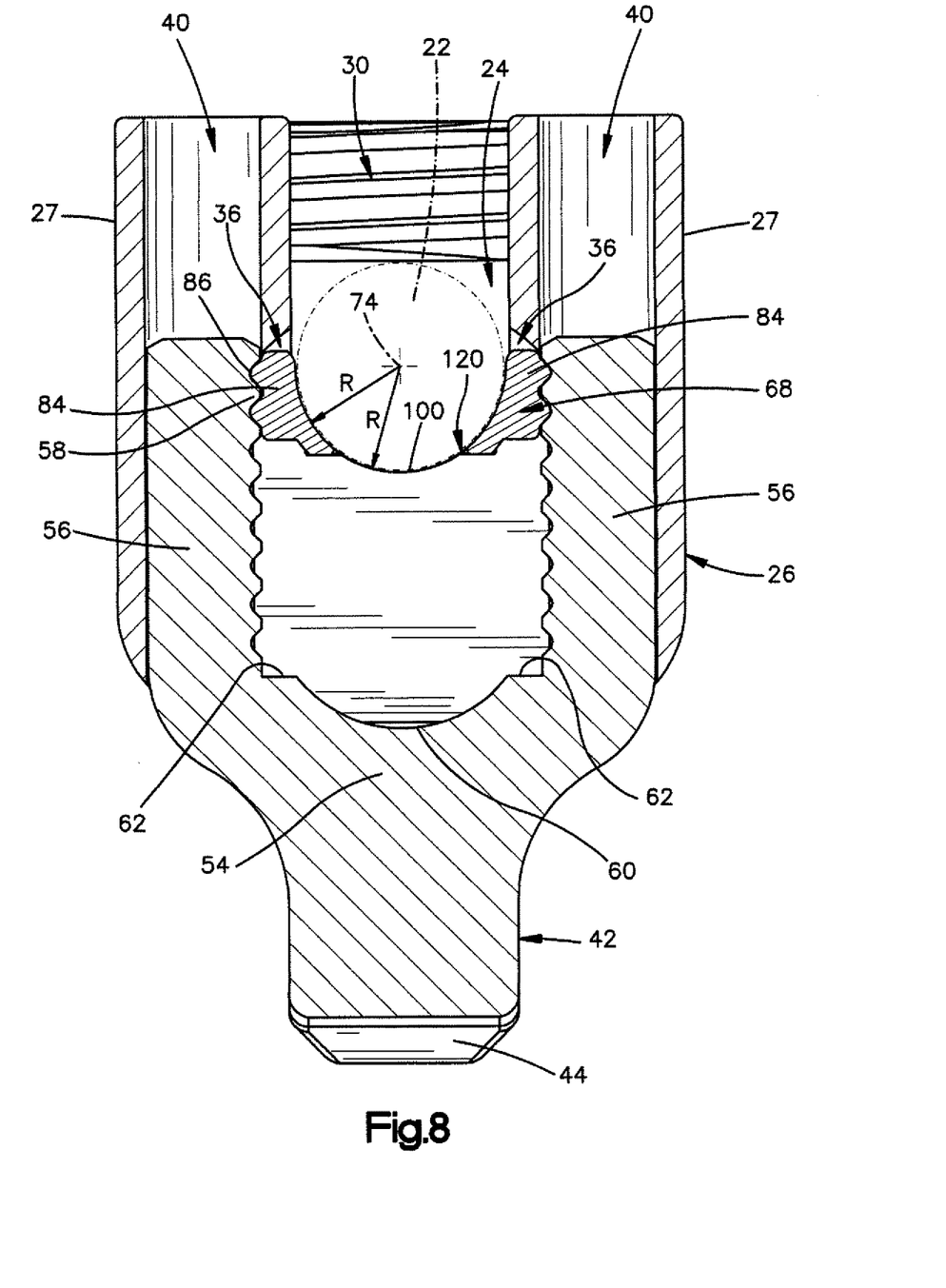
FIG. 8 is a sectional view taken along line 8-8 of FIG. 1.

As shown in FIG. 1, to assemble the apparatus 20, the extensions 56 of the connector 42 are inserted through the lower surface 38 of the housing 26 and into the openings 40 in the side walls 27 in the manner indicated generally by arrow A (see also FIG. 8). Inserting the extensions 56 into the openings 40 aligns the central portion 54 of the connector 42 with the slot 36 in the housing 26. The extensions 56 of the connector 42 are oriented such that the upper surface 46 of the base 44 faces the lower surface 38 of the housing 26 when the connector is inserted into the openings 40. The connector 42 may freely move or slide within the openings 40 and relative to the housing 26 to move the upper surface 46 of the connector relative to the lower surface 38 of the housing into any one of a plurality of desired positions. Accordingly, the connector 42 moves relative to the housing 26 in directions extending through the upper and lower surfaces 28, 38 and transverse to the axis 29 to move the base 44 toward and/or away from the housing.

Alternatively, the connector 42 may be inserted into the housing 26 such that the base 44 is not aligned with the lower surface 38 of the housing 26 (not shown). For example, the connector 42 may be rotated 180° from the position shown in FIG. 1 such that the base 44 extends in a direction opposite the direction shown in FIG. 1.

The housing 26 may include recesses and/or projections (not shown) that are engagable with surgical instruments for holding the housing during insertion and/or adjustment of the connector 42. The recesses and/or projections may also be used for connecting the housing 26 and connector 42 to the vertebra.

When the extensions 56 of the connector 42 are positioned within the openings 40 in the housing 26, at least one tooth of the teeth 58 on each extension are aligned with the slot 36 formed in the side walls 27 of the housing. In this configuration, the teeth 58 on each arm 56 extend inwardly toward the passage 24 and into the slot 36. The teeth 58 on the extensions 56 are therefore accessible via the passage 24 in the housing 26 when aligned with the slot 36.

The connector 42 moves or slides relative to the housing 26 in the manner designated by arrow A until one or more of the teeth 58 on the extensions 56 are exposed through the slot 36. The locking member 68 is then inserted into the recess 41 in the housing 26 by deflecting the arms 72 toward each other so that the arms are spaced closer together than the gap between the side walls 27 of the housing. More specifically, while inwardly deflecting the arms 72 of the locking member 68, the base portion 70 is positioned within the arcuate portion 43 of the recess 41 and each arm 72 is positioned within a straight portion 45 of the recess. This aligns the locking portion 84 at the end of each arm 72 with a portion of the slot 36 in each side wall 27. More specifically, the outwardly facing teeth 86 on the locking portions 84 are aligned with and face a portion of the slot 36 in each side wall 27.

When the inward deflection force on the arms 72 of the locking member 68 is removed or released, the locking member returns to its natural or unstressed state and the teeth 86 on the locking portion 84 move outward towards the side walls 27, into the slot 36, and into engagement with the exposed teeth 58 on the connector 42. The arms 72 of the locking member 68 therefore snap into engagement with the extensions 56 of the connector 42, thereby holding the connector in a single position relative to the housing.

In this configuration, the concave surface 100 of the housing 24 and the concave surfaces 88, 90, 92 of the locking member 68 are all aligned to form a substantially smooth, uniform surface 102. The contour of the side walls 27 adjacent to the concave surface 100 may also be curved and form part of the surface 102. Regardless, the contour of the surface 102 substantially corresponds with the periphery of the rod 22.

Snapping the locking member 68 into engagement with the connector 42 holds the upper surface 46 of the connector 42 at a desired distance indicted by D (FIG. 1) from the lower surface 38 of the housing 26. The bone or vertebra is positioned between the upper surface 46 of the connector 42 and the lower surface 38 of the housing 26. The connector 42 may be moved relative to the housing 26 to fit the vertebra or other anatomic structure between the connector and the housing. In particular, the position of the connector 42 relative to the housing 26 may be manually adjusted while the locking member 68 engages the extensions 56 of the connector and the recess 41 in the housing by applying a first predetermined force to the connector relative to the housing.

If a sufficient force is applied to the connector 42 relative to the housing 26 while the locking member 68 engages the housing and the connector, the teeth 58 on the connector cause the arms 72 of the locking member 68 to deflect inwardly toward each other and away from the teeth on the connector. The inward movement of the arms 72 relative to the extensions 56 reduces the engagement between the teeth 58, 84 and allows the connector 42 to move relative to the locking member 68 and the housing 26. More specifically, as the connector 42 moves, the teeth 86 on the locking member 68 snap or ratchet into and out of engagement with successive teeth 58 on the extensions 56 of the connector.

Once the connector 42 is in the desired position relative to the housing 26 with the vertebra between the lower surface 38 of the housing and the upper surface 46 of the connector, the first predetermined force is removed from the connector. This allows the teeth 86 on the arms 72 to deflect outwardly into full engagement with the teeth 58 on the connector 42, thereby holding the connector in the desired position relative to the housing. The first predetermined force may thereafter be applied to the connector 42 any number of times to reposition or re-adjust the connector relative to the housing 26, if desired. The connector 42 may be moved relative to the housing 26 until the locking portions 84 engage the teeth 58 closest to the central portion 54 of the connector 42. At this point, the locking portions 84 abut the stop surfaces 62 on the connector 42, placing the concave surface 60 of the central portion 54 in alignment with the concave surface 100 of the housing 26. The concave surface 60 of the central portion 54 thereby forms part of the uniform surface 102.

The size, spacing, and number of mating teeth 58, 86 on the connector 42 and the locking member 68, respectively, dictate the number of positions as well as the precision of the position in which the connector may be held by the locking member relative to the housing. Therefore, the configuration of the mating teeth 58, 86 may be tailored to meet desired performance criteria.

The rod 22 is positioned along the axis 29 within the passage 24 of the housing 26 and is moved towards the concave surface 100 until the rod overlies the surface 102. When the rod 22 engages the surface 102, the locking portions 84 of the locking member 68 engage the periphery of the rod. The rod 22 and/or the arms 72 may be sized or shaped such that the rod causes the arms to outwardly deflect away from one another when the rod is fully engaged with the locking portions 84.

Prior to the clamping member 30 being connected to the housing 26, the rod 22 may move within the passage 24 and, thus, the rod may move into and out of engagement with the locking portions 84 of the locking member 68. When the rod 22 is within the passage 24 but spaced from the locking portions 84, the application of force to the connector 42 relative to the housing 24 causes the connector to move as the connector ratchets with the locking member in the manner described.

Even if the locking portions 84 are partially or fully engaged with the rod 22, the connector 42 may be moved relative to the housing 26 prior to the clamping member 30 being threaded onto the housing. Since the concave inner surfaces 88 on the locking portions 84 of the arms 72 are contoured to match the periphery of the rod 22, inward movement of the arms toward one another causes the rod to be lifted upward away from the surface 102. Inward movement of the arms 72 is accomplished by applying a second predetermined force to the connector 42 relative to the housing 26. The second predetermined force is larger than the first predetermined force because the locking portions 84 of the locking member 68 overcome the resistance to inward movement of the arms 72 caused by the positioning of the rod 22 on the locking member. Therefore, prior to the clamping member 30 being connected to the housing 26, the application of the second predetermined force to the connector 42 causes the connector to ratchet with the locking member 68 in the manner described, causing inward and outward deflection of the arms 72 and, thus, up and down movement of the rod 22 relative to the locking portions 84 while the connector moves relative to the housing into the desired position.

The clamping member 30 is threaded onto the housing 26 to prevent the rod 22 from moving out of the passage 24. Where the housing 26 exhibits a tubular shape, the clamping member 30 may be threaded into a threaded bore that extends through the upper surface 28 of the housing 26 and into the passage 24 (not shown). Rotation of the clamping member 30 in the first direction relative to the housing 26 causes the clamping member to move toward the concave surface 100 while rotation of the clamping member in the second, opposite direction relative to the housing causes the clamping member to move away from the concave surface. The clamping member 30 may be moved toward the concave surface 100 to lock rod 22 and the connector 42 relative to the housing 26.

The connector 42 is movable relative to the housing 26 in the manner described as long as the distance between the clamping member 30 and the locking member 68 is sufficient to allow the rod 22 to move between the clamping member and the locking member. In other words, the connector 42 is movable relative to the housing 26 while the clamping member 30 is connected to the housing so long as the rod 22 can still move out of full engagement with the locking portions 84 of the locking member 68. Accordingly, the clamping member 30 may retain the rod 22 within the housing 26 while allowing relative movement between the housing, the rod, and the connector 42. In such a case, the application of the second predetermined force to the connector 42 causes the rod 22 to move up and down relative to the locking portions 84 as the arms 72 of the locking member 68 ratchet, i.e., deflect inwardly and outwardly, with the extensions 56 of the connector to allow the connector to move relative to the housing into the desired position.

Although the rod 22 is shown as being connected to the housing 26 with the threaded clamping member 30, it is contemplated that the rod 22 may be connected to the housing in any desired manner. It is contemplated that the rod 22 may be connected to the housing 26 by a threaded cap, a cap that slidably engages the housing and pushes the rod into the passage, a clamping member that extends at a different angle than the angle shown, a cap that is press fit into the housing or by deforming or swaging the housing (not shown).

Once the connector 42 is in a desired position relative to the housing 26, the clamping member 30 is operated to lock the connector into the desired position. More specifically, the clamping member 30 is rotated until it engages the rod 22 to lock the position of the rod against the surface 102 by clamping the rod between the surface and the clamping member. In this condition, the rod 22 maintains the locking portions 84 of the locking member 68 in engagement with the extensions 56. This prevents the locking portions 84 from deflecting inwardly toward one another and thereby prevents the teeth 86 of the locking member 68 from ratcheting with the teeth 58 on the extensions 56 of the connector 42. Accordingly, the connector 42 is prevented from moving out of the desired position relative to the housing 26. The threaded connection between the clamping member 30 and the side walls 27 of the housing 26 therefore securely interconnects the rod 22, the housing 26, the locking member 68, and the connector 42 together, thereby preventing relative movement between the rod, the housing, the locking member, and the connector.

Although the sequence of assembling the vertebral fixation device of the present invention is described in a particular way, it will be appreciated that the present invention may be assembled in a different order. For example, the locking member 68 may be positioned within the recess 41 of the housing 26 prior to inserting the connector 42 into the openings 40 in the side walls 27. Furthermore, the clamping member 30 may be threadably engaged with the housing 26 prior to inserting the locking member 68 into the recess 41 and/or inserting the rod 22 into the passage 24.

The vertebral fixation device of the present invention advantageously alleviates the need to produce a wide range of connectors and housings to accommodate various pathologies, anatomies, and vertebral levels. In particular, the ability to adjust and lock the connector 42 in any number of positions relative to the housing 26 allows the vertebral fixation device of the present invention to be used in a wide range of spinal fixation applications while minimizing the number of parts required. Furthermore, the ratcheting connection between the deflectable locking member 68 and the connector 42 facilitates rapid in vivo or ex vivo adjustment of the vertebral fixation device. Moreover, the cooperation between the clamping member 30, the rod 22, and the locking member 68 provides a secure connection between the housing 26 and the connector 42 and reduces the likelihood that the connector will move relative to the housing once the vertebral fixation device is secured to the vertebrae.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for use in retaining bone in a desired spatial relationship, the apparatus comprising:
  a rod;
  a housing having a passage through which the rod extends along an axis;
  a connector that extends from the housing and is configured to engage a bone, the connector being movable linearly relative to the housing toward and away from the axis in a direction extending transverse to the axis into any one of a plurality of positions; and
  a locking member deflectable between a first condition for allowing relative movement between the connector and the housing and a second condition engaging the connector to hold the connector in any one of the plurality of positions relative to the housing.

2. The apparatus recited in claim 1, wherein the connector includes a first plurality of teeth and the locking member includes a second plurality of teeth that mate with the first plurality of teeth to hold the connector in any one of the plurality of positions.

3. The apparatus recited in claim 2, wherein the application of a predetermined force to the connector when the locking member is in the second condition causes the connector to move relative to the housing from a first position of the plurality of positions to a second position of the plurality of positions, the locking member moving from the second condition toward the first condition in response to application of the predetermined force, the locking member holding the connector in the first position and the second position.

4. The apparatus of claim 3, wherein the locking member includes at least one deflectable arm that engages the connector, the application of the predetermined force to the connector deflecting the at least one arm to allow the connector to move between the first and second positions.

5. The apparatus of claim 4, wherein the locking member includes a pair of deflectable arms that engage the connector, the application of the predetermined force to the connector urging the arms toward one another to allow the connector to move between the first and second positions.

6. The apparatus of claim 1, wherein the locking member snaps into engagement with the connector to hold the connector in any one of the plurality of positions relative to the housing.

7. The apparatus of claim 1, wherein the locking member is a spring member.

8. The apparatus recited in claim 1, wherein the locking member is movable into the passage in a direction substantially parallel to the axis from a first position spaced from the connector to a second position in which a portion of the locking member engages the connector.

9. The apparatus recited in claim 1, wherein the housing includes openings for receiving extensions of the connector and a slot that connects the passage with at least one of the openings, a portion of the locking member extending through the slot and into the at least one opening to engage the connector and hold the connector in any one of the plurality of positions relative to the housing.

10. The apparatus recited in claim 9, wherein the locking member includes at least one deflectable arm that engages the connector to hold the connector in any one of the plurality of positions relative to the housing.

11. The apparatus recited in claim 10, wherein the locking member includes a pair of deflectable arms that extend along opposing sides of the passage in the housing, each arm engaging the connector to hold the connector in any one of the plurality of positions relative to the housing.

12. The apparatus recited in claim 1, wherein the locking member has a third condition preventing relative movement between the connector and the housing.

13. The apparatus recited in claim 12, further comprising a clamping member that cooperates with the housing to secure the rod within the passage, the clamping member being movable relative to the housing from a first position connected to the housing such that the connector is movable relative to the housing to a second position in which the rod engages the locking member to place the locking member in the third condition preventing relative movement between the connector and the housing.

14. The apparatus recited in claim 13, wherein the locking member includes at least one deflectable arm that engages the connector to prevent relative movement between the connector and the housing when the locking member is in the third condition.

15. The apparatus recited in claim 14, wherein the rod holds the at least one arm of the locking member in an outwardly deflected position engaged with the connector when the clamping member is in the second position to prevent relative movement between the connector and the housing.

16. The apparatus recited in claim 15, wherein the connector includes a first plurality of teeth and each arm of the locking member includes a second plurality of teeth that mate with the first plurality of teeth to prevent relative movement between the connector and the housing when the locking member is in the third condition.

17. An apparatus for use in retaining bone in a desired spatial relationship, the apparatus comprising:
  a rod;
  a housing having a passage through which the rod extends;
  a connector that extends from the housing and is configured to engage a bone, the connector being movable linearly relative to the housing into any one of a plurality of positions; and
  a locking member extending within the passage, the locking member having a first condition allowing relative movement between the connector and the housing, a second condition releasably holding the connector in any one of the plurality of positions relative to the housing, and a third condition preventing the connector from moving relative to the housing.

18. The apparatus recited in claim 17, wherein the locking member includes at least one deflectable arm, the rod urging the at least one arm into engagement with the connector when the rod is within the passage of the housing to place the locking member in the third condition.

19. The apparatus recited in claim 18, wherein the application of a predetermined force to the connector when the locking member is in the second condition causes the connector to move relative to the housing from a first position of the plurality of positions to a second position of the plurality of positions, the locking member holding the connector in the first position and the second position.

20. The apparatus recited in claim 18, further comprising a clamping member that cooperates with the housing to secure the rod within the passage, the clamping member being movable relative to the housing from a first position connected to the housing such that the connector is movable relative to the housing to a second position in which the rod engages the locking member to place the locking member in the third condition preventing relative movement between the connector and the housing.

21. The apparatus recited in claim 17, wherein the locking member is a deflectable spring member.

22. An apparatus for use in retaining bone in a desired spatial relationship, the apparatus comprising:
a rod;
a housing having a passage through which the rod extends along an axis;
a connector that extends from the housing and is configured to engage a bone, the connector being movable relative to the housing in opposite directions into any one of a plurality of positions; and
a locking member engaging the connector to releasably hold the connector in any one of the plurality of positions, the connector being movable in the opposite directions to any of the plurality of positions by applying a predetermined force to the connector, the locking member having a first condition for allowing relative movement between the connector and the housing and a second condition engaging the connector to hold the connector in any one of the plurality of positions relative to the housing, the application of the predetermined force to the connector to move the connector in either of the opposite directions when the locking member is in the second condition causes the locking member to move relative to the housing from the second condition toward the first condition and the connector to move relative to the housing from a first position of the plurality of positions to a second position of the plurality of positions, the locking member holding the connector in the first position and the second position.

23. The apparatus recited in claim 22, wherein the connector includes a first plurality of teeth and the locking member includes a second plurality of teeth that mate with the first plurality of teeth to hold the connector in any one of the plurality of positions.

24. The apparatus recited in claim 22, wherein the locking member is deflectable from the first condition for allowing relative movement between the connector and the housing to the second condition engaging the connector to hold the connector in any one of the plurality of positions relative to the housing.

25. The apparatus of claim 24, wherein the locking member includes at least one deflectable arm that engages the connector, the application of the predetermined force to the connector deflecting the at least one arm to allow the connector to move between the first and second positions.

26. The apparatus of claim 24, wherein the locking member includes a pair of deflectable arms that engage the connector, the application of the predetermined force to the connector urging the arms toward one another to allow the connector to move between the first and second positions.

27. The apparatus recited in claim 24, wherein the locking member has a third condition preventing relative movement between the connector and the housing.

28. The apparatus recited in claim 27, further comprising a clamping member that cooperates with the housing to secure the rod within the passage, the clamping member being movable relative to the housing from a first position connected to the housing such that the connector is movable relative to the housing to a second position in which the rod engages the locking member to place the locking member in the third condition preventing relative movement between the connector and the housing.

29. The apparatus recited in claim 28, wherein the locking member includes at least one deflectable arm that engages the connector to prevent relative movement between the connector and the housing when the locking member is in the third condition.

30. The apparatus recited in claim 29, wherein the rod holds the at least one arm of the locking member in an outwardly deflected position engaged with the connector when the clamping member is in the second position to prevent relative movement between the connector and the housing.

31. The apparatus recited in claim 30, wherein the connector includes a first plurality of teeth and each arm of the locking member includes a second plurality of teeth that mate with the first plurality of teeth to prevent relative movement between the connector and the housing when the locking member is in the third condition.

32. The apparatus of claim 22, wherein the locking member snaps into engagement with the connector to hold the connector in any one of the plurality of positions relative to the housing.

33. The apparatus of claim 22, wherein the locking member is a spring member.

34. The apparatus recited in claim 22, wherein the locking member is movable into the passage in a direction substantially parallel to the axis from a first position spaced from the connector to a second position in which a portion of the locking member engages the connector.

35. The apparatus recited in claim 22, wherein the housing includes openings for receiving extensions of the connector and a slot that connects the passage with at least one of the openings, a portion of the locking member extending through the slot and into the at least one opening to engage the connector and hold the connector in any one of the plurality of positions relative to the housing.

36. The apparatus recited in claim 35, wherein the locking member includes at least one deflectable arm that engages the connector to hold the connector in any one of the plurality of positions relative to the housing.

37. The apparatus recited in claim 36, wherein the locking member includes a pair of deflectable arms that extend along opposing sides of the passage in the housing, each arm engaging the connector to hold the connector in any one of the plurality of positions relative to the housing.

38. The apparatus recited in claim 22, wherein the connector is linearly movable relative to the housing into any one of the plurality of positions.

* * * * *